United States Patent [19]

Tweedle

[11] 4,455,291
[45] Jun. 19, 1984

[54] ACCELERATORS FOR FORMING CATIONIC TECHNETIUM COMPLEXES USEFUL AS RADIODIAGNOSTIC AGENTS

[75] Inventor: Michael F. Tweedle, North Chelmsford, Mass.

[73] Assignee: New England Nuclear Corporation, Boston, Mass.

[21] Appl. No.: 341,553

[22] Filed: Jan. 22, 1982

[51] Int. Cl.$^3$ .................. A61K 43/00; A61K 49/00; C07F 9/66; C07F 9/90
[52] U.S. Cl. .................. 424/1.1; 260/429 R; 260/440; 260/446; 424/9
[58] Field of Search ............ 260/429 R, 440, 446; 568/2, 8, 13–17; 424/1, 1.5, 9

[56] References Cited

U.S. PATENT DOCUMENTS

| | | |
|---|---|---|
| 2,587,805 | 3/1952 | Akobjanoff .................. 260/440 |
| 3,188,345 | 6/1965 | Burg et al. .................. 568/2 |
| 3,478,035 | 11/1969 | Barrett .................. 564/19 |
| 3,478,036 | 11/1969 | Winkelmann et al. .................. 564/19 |
| 3,798,241 | 3/1974 | Kagan et al. .................. 260/446 |
| 3,819,670 | 6/1974 | Kemp .................. 260/440 |
| 3,987,157 | 10/1976 | Molinski et al. .................. 424/1 |
| 4,042,676 | 8/1977 | Molinski et al. .................. 424/1 |
| 4,042,677 | 8/1977 | Molinski et al. .................. 424/1 |
| 4,057,615 | 11/1977 | Bardy et al. .................. 424/1 |
| 4,133,872 | 1/1979 | Schmidt-Dunker et al. .................. 424/1 |
| 4,229,427 | 10/1980 | Whitehouse .................. 424/1 |
| 4,247,534 | 1/1981 | Bevan .................. 424/1 |
| 4,338,248 | 7/1982 | Yokoyama et al. .................. 424/1 |
| 4,363,793 | 12/1982 | Blau et al. .................. 424/1 |
| 4,374,821 | 2/1983 | Glavan et al. .................. 260/429 R |

FOREIGN PATENT DOCUMENTS 38756 10/1981 European Pat. Off. .................. 424/1

OTHER PUBLICATIONS

Deutsch et al., J. Nucl. Mfo., vol. 22 (Oct. 1981): 897–907.
Friesen, D. K. et al., J. of Molecular Structure, 31 (1976) 77–95.
Communications to the Editor, J. Am. Chem. Soc., 1980, vol. 102, No. 22, 1980 pp. 6849–6851.
Zsuzsa Nagy-Magos et al., J. of Organometallic Chemistry, 171 (1979) 97–102.
Akhtar, M., et al. Inorganic Chemistry, vol. 11, No. 12, 1972 pp. 2917–2921.
Communications to the Editor, J. Am. Soc., 101, 1979 pp. 1053–1054.
Brown, L. D., et al. Inorganic Chemistry, vol. 17, No. 3, 1978 pp. 720–734.
Albright, J. O., et al. J. Am. Chem. Soc., 101, 1979) 611–619.
Kyba, E. P., et al., J. Am. Chem. Soc., vol. 102, No. 23, 1980 pp. 7012–7014.
Butter, S. A., et al. J. Am. Chem. Soc. (1970) pp. 1411–1415.
Inoue, Y., et al., Bulletin of the Chem. Soc. of Japan, vol. 51(B), (1978) pp. 2375–2378.
Chatt, J., et al., J. Chem. Soc., (1961) pp. 896–904.
Mazzi, U., et al., Inorganic Chemistry, vol. 16, No. 5, 1977 pp. 1042–1048.
Chatt, J., et al. J. Chem. Soc., (1962) pp. 2545–2549.
Ferguson, J. E. et al., Aust. J. Chem., 1970, 23, 453–461.
King, R. B., Acc. Chem. Res. 1980, 13, pp. 243–248.
Wymore, C. E., et al., J. Inorg. Nucl. Chem., 1980, vol. 14, pp. 42–54.
Ferguson, J. E., et al., J. Inorg. Nucl. Chem., 1966, vol. 28, pp. 2293–2296.
Cooper, P., et al., J. Chem. Soc., (C) (1971) pp. 3031–3035.
Subramanian, Gopal et al., Proceedings of the 28th Annual Meeting, Los Vegas Jun. 16–19, 1981, vol. 22, No. 6, p. 51.
Deutsch, E. et al. Science, vol. 214, (1981) pp. 85–86.
Ferguson, J. E. et al., Chemistry and Industry, Nov. 22, 1958, p. 1555.
Curtis, N. F., Chemistry and Industry, May 24, 1958, pp. 625–626.
Communications to the Editor, J. Am. Chem. Soc., 97 (1975) pp. 1955–1956.
Bandoli, G. et al., J.C.S. Dalton (1976) pp. 125–130.
Viard, B., J. Inorg. Nucl. Chem., 1977, vol. 39, pp. 1090–1092.
Fergusson et al., Chemistry and Industry, pp. 347–348.

*Primary Examiner*—Christine M. Nucker
*Attorney, Agent, or Firm*—Sewall P. Bronstein; George W. Neuner

[57] ABSTRACT

A composition for preparing cationic lipophilic technetium complexes is described. The composition comprises an admixture of (a) an accelerator compound selected from the group of water-soluble organic bidentate ligands that are capable of coordinating with technetium to form a 4 to 6 member ring and (b) a target-seeking ligand, or aqueous salt thereof, having the structure indicated in formulas I, II or III. The accelerator compound has a weaker coordinating bond with technetium than the target-seeking ligand has with technetium.

33 Claims, No Drawings

ACCELERATORS FOR FORMING CATIONIC TECHNETIUM COMPLEXES USEFUL AS RADIODIAGNOSTIC AGENTS

FIELD OF THE INVENTION

The present invention relates to compositions for making cationic radiodiagnostic agents and, in particular, to accelerators for labelling such cationic radiodiagnostic agents, kits for preparing such $^{99m}$Tc-labelled cationic radiodiagnostic agents with technetium, and methods for labelling such cationic radiodiagnostic agents with technetium.

BACKGROUND OF THE INVENTION

Various complexes of monodentate and bidentate ligands with technetium have been made and studied. These complexes generally were made for use in studies to determine the various oxidation states of technetium and for other research regarding the structure of such complexes and metal-coordination chemistry. Such studies have been reported in, for instance, *Chemistry and Industry*, pp. 347–8 Mar. 26, 1960); *J. Inorg. Nucl. Chem.*, Vol. 28, pp 2293–96 (1966); *Aust. J. Chem.*, 23, pp 453–61 (1970); *Inorganic Chem.*, vol. 16, No. 5, pp. 1041–48 (1977), *J. Inorg. Nucl. Chem.*, Vol. 39, pp. 1090–92 (1977); and *J. C. S. Dalton*, pp. 125–30 (1976).

Recently, in a presentation to the American Pharmaceutical Association, E. A. Deutsch disclosed that certain complexes of DIARS, i.e.

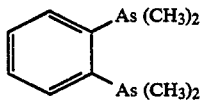

and Tc-99m, and certain complexes of DMPE, i.e. $(CH_3)_2 PCH_2CH_2P(CH_3)_2$, and Tc-99m may be useful as radiodiagnostic agents for myocardial or hepatobiliary imaging. $[^{99m}Tc-(DMPE)_2Cl_2]^+$ and $[^{99m}Tc-(DIARS)_2Br_2]^+$ were prepared by Deutsch by heating in an open flask a reaction mixture containing the appropriate hydrogen halide in aqueous alcohol solution, $^{99m}$Tc-sodium pertechnetate, and ortho-phenylenebis(dimethylarsine), i.e. DIARS, or bis-(1,2-dimethylphosphino)ethane, i.e. DMPE. The reaction was reported to take about 30 minutes. The labelled complex was then purified by chromatographic methods involving ion exchange columns.

The labelled complex produced according to the procedure of Deutsch has several practical disadvantages. The procedure requires handling several ingredients including an organic solvent to make the reaction mixture and then purifying the resulting radiolabelled complex by chromatography. Each of these handling steps can contaminate the system and final product. The purification step further requires additional time for preparation of the final product. These steps require a stilled technician and are performed at the site of use, just prior to use. Thus, a complex, time consuming chemical preparation is required during which sterility of ingredients and containers is difficult to maintain. Thus, to assure freedom from contamination, a final sterilization step is required, which further adds to preparation time. Because Tc-99m has a short half-life, lengthy preparation methods are undesirable. Thus, the complexity of the preparation, both with regard to maintaining sterile conditions and to purification of the $^{99m}$Tc-labelled complex make the Deutsch procedure undesirable.

It would be highly desirable to have a sterilized kit with all the necessary materials prepared by the manufacturer, to which only the Tc-99m need be added at the site of use to produce the desired labelled complex directly in high enough yield to obviate the need for purification. It would also be desirable for the kit materials to be in a closed container or vial, pre-sterilized, so that the only step to be performed at the site of use would be the addition of the radionuclide. To increase stability and shelf-life of the kit, it would be highly desirable that the materials be readily lyophilized, preferably from an aqueous solution.

By achieving the desirable features outlined above, a convenient-to-use heart imaging radiopharmaceutical agent would be provided that is capable of concentrating in healthy heart tissue to provide a negative image of an infarct, or damaged or ischemic tissue.

A copending application, Ser. No. 311,770, filed Oct. 15, 1981 in the name of Vinayakam Subramanyam, which is hereby incorporated by reference, describes an acid salt of a mono or polydentate ligand that is water soluble, stable in a lyophilized state, and is capable of binding with Tc-99m to form a cationic complex. The acid salt may be generally represented by the formula:

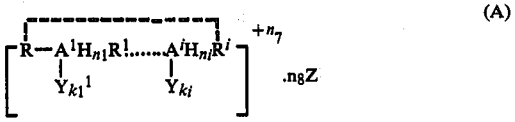

(A)

wherein:
i is an integer from 1 to 6;
R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;
$Y^1$, $Y^2$, $Y^3$, $Y^4$, $Y^5$ and $Y^6$ are independently selected from substituted or unsubstituted alkyl, aryl, alkylaryl, arylalkyl, monocycloalkyl, polycycloalkyl, heterocyclic and carbocyclic groups;
$A^1$, $A^2$, $A^3$, $A^4$, $A^5$ and $A^6$ are the same or different neutral donor atoms, each having a free-electron pair available for accepting a proton to provide a charged ligand or for complexing with Tc-99m or Tc-99 to form a cationic complex;
Z is preferably a parenterally acceptable anion;
$k_1$, $k_2$, $k_3$, $k_4$, $k_5$ and $k_6$ are each independently zero or one;
$n_1$, $n_2$, $n_3$, $n_4$, $n_5$ and $n_6$ are independently 0 or 1; and $n_7$ and $n_8$ are integers from 1 to 6 where $$n_7 = \sum_{i=1}^{6} n_i$$

and the charge represented by $n_8Z$ is equal in magnitude and opposite in sign to $+n_7$; or

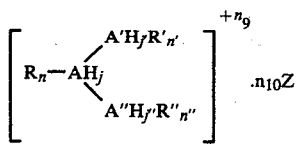  (B)

wherein:
R, R' and R" are independently selected from hydrogen or substituted or unsubstituted alkyl, aryl, alkylaryl, arylalkyl, monocylcloalkyl, polycycloalkyl, heterocyclic and carbocyclic groups;
A, A' and A" are independently selected from the group of neutral donor atoms having a pair of electrons available for accepting a proton to provide a charged ligand or for complexing with Tc-99m or Tc-99 to form a cationic complex;
j, j' and j" are independently 0 or 1;
n, n' and n" are independently the integer 1 or 2;
Z is the same as defined above
$n_9$ and $n_{10}$ are integers selected from 1 to about 3, where $n_9 = j + j' + j''$ and the charge represented by $n_{10}Z$ is equal in magnitude and opposite in sign to $+n_9$.

These acid salts are normally solid compounds, water-soluble, readily lyophilized, and capable of reducing pertechnetate and binding with technetium to form stable cationic complexes.

Cationic technetium complexes of these acid salts, useful for radiodiagnostic treatments, are prepared for mixing the acid salt and $^{99m}$Tc-pertechnetate in an aqueous or alcoholic solution and heating the mixture to form the cationic complex. Preferably, the ligand is provided as a lyophilized ligand acid salt as described by V. Subramanyam in copending application Ser. No. 311,770 and is contained in a sealed, sterilized vial prior to adding the pertechnetate. The pertechnetate solution can then be injected into the vial under aseptic conditions to maintain sterility. To obtain high yields, the vial is generally heated and maintained at an elevated temperature for sufficient time to form a complex of the ligand with technetium. The vial should preferably be heated to at least 80° C. for a suitable length of time, i.e. about 30 minutes or more at 80° C. Preferably, the vial is heated to 100° C. or more, and more preferably to a temperature in the range of from about 130° C. to about 150° C. At about 150° C., the reaction can be completed in about five to ten minutes, depending upon the choice and concentrations of the reactants. After cooling, the resulting radiopharmaceutical preparation may be adjusted for pH and is ready for use. Typically, when the pH is adjusted, it is adjusted into the range of from about 4.0 to about 9.0, and preferably to physiological pH.

It is desirable to obtain high yields of the cationic technetium complexes for radiodiagnostic uses in one step without the need for purification of the labelled compound. It is also desirable to obtain these high yields using temperatures of 100° C. or less because constant temperature water baths are readily available in clinical laboratories.

SUMMARY OF THE INVENTION

The present invention provides compositions and kits for preparing cationic technetium labelled complexes using ordinary laboratory water baths for heating. The composition and kits of this invention comprise (1) an accelerator compound selected from the group of bidentate ligands capable of forming a stable four to six member ring with technetium and (2) a target-seeking ligand having the structural formula:

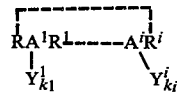  I wherein
i is an integer from 1 to 6;
R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;
$Y^1$, $Y^2$, $Y^3$, $Y^4$, $Y^5$ and $Y^6$ are independently selected from substituted or unsubstituted alkyl, aryl, alkylaryl, arylalkyl, monocycloalkyl, polycycloalkyl, heterocyclic and carbocyclic groups;
$A^1$, $A^2$, $A^3$, $A^4$, $A^5$ and $A^6$ are the same or different neutral donor atoms, each having a free-electron pair available for complexing with Tc-99m or Tc-99 to form a cationic complex; and
$k_1$, $k_2$, $k_3$, $k_4$, $k_5$ and $k_6$ are each independently zero or one;

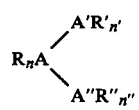  II wherein:
R, R' and R" are independently selected from hydrogen or substituted or usubstituted alkyl, aryl, alkylaryl, arylalkyl, monocylcloalkyl, polycycloalkyl, heterocyclic and carbocyclic groups;
A, A' and A" are independently selected from the group of neutral donor atoms having a pair of electrons available for complexing with Tc-99m or Tc-99 to form a cationic complex; and
n, n' and n" are independently the integer 1 or 2; or

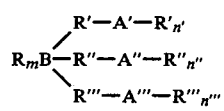  III wherein
R, R', R" and R'" are independently selected from hydrogen or substituted or unsubstituted alkyl, aryl, alkylaryl, arylalkyl, monocylcloalkyl, polycycloalkyl, heterocyclic and carbocyclic groups;
A', A" and A'" are independently selected from the group of neutral donor atoms having a pair of electrons available for complexing with Tc-99m or Tc-99 to form a cationic complex;
B is an atom selected from the group of neutral donor atoms having a pair of electrons available for complexing with Tc-99m or Tc-99 or from the elements listed in Group IV A of the periodic table (i.e. C, Si, Ge, Sn, and Pb);
m is 0 is 1;
n', n" and n'" are independently the integer 1 or 2;

wherein the technetium coordinate bond with said bidentate accelerator ligand is weaker than the technetium coordinate bond with said target-seeking ligand.

Preferably the bidentate accelerator ligand is capable of reducing technetium. In one embodiment, the bidentate ligand is capable of forming coordinate bonds with technetium through oxygen atoms. In a preferred embodiment of this invention, the composition and kit are useful for preparing technetium labelled complexes in yield high enough to be useful for radiodiagnostic agents using ordinary water baths for heating and without the need for purification.

The compositions of this invention comprising the accelerator compound and target-seeking ligand are preferably supplied as a kit as lyophilized solids in a pre-sterilized vial. Useful cationic technetium complexes are prepared in accord with this invention, for example, by adding $^{99m}$Tc-pertechnetate solution to the vial and heating in a water bath to obtain high yields of the desired complexes.

The R's in formulas I, II and III are preferably alkyl radicals having 1 to about 6 carbon atoms such as methyl, ethyl, etc., and the like, and aryl radicals such as benzyl, phenyl, etc., and the like.

The cationic complexes formed from compositions and kits of this invention, when radiolabelled are useful for radiodiagnostic tests in connection with myocardial and hepatobiliary tissues.

DETAILED DESCRIPTION OF THE INVENTION

The compositions and kits of the present invention can be prepared from a wide variety of monodentate and polydentate target-seeking ligands. Typical examples of such ligands include, for instance, aryl compounds having arsenic, phosphorus, nitrogen, sulfur, oxygen, selenium, tellurium, or any combination of them, substituted ortho to each other. For example, o-phenylene compounds having the structure:

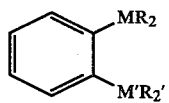   IV in which M and M' are arsenic, phosphorus, nitrogen, sulfur, oxygen, selenium, tellurium, or any combination of them, and R and R' are independently hydrogen, or an organic group, preferably an alkyl group having 1 to 6 carbon atoms, an aryl group such as phenyl, or the like, and substituted such groups. Additional examples of suitable target-seeking ligands include bidentate cis-tetraethylene ligands of the formula:

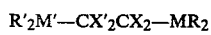   V in which M, M', R, and R' are as defined above and X and X' are independently selected from hydrogen, halide, or substituted or unsubstituted lower alkyl groups having 1 to about 6 carbon atoms. Further examples of suitable target-seeking ligands include those having the formula:

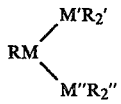   VI where M, M', R, and R', are as defined above, M" is independently selected from arsenic, phosphorous, nitrogen, sulfur, oxygen, selenium, and tellurium, and R" is independently selected from hydrogen, halide or an organic radical, preferably an alkyl radical having 1 to about 6 carbon atoms, an aryl radical such as phenyl, or the like, and substituted such groups.

Particularly preferred target-seeking ligands for the practice of this invention are the bis-dialkylphosphinoethanes and their substituted derivatives, including, for example,
1,2-bis(dimethylphosphino)ethane,
1,2-bis(di(trifluoromethyl)phosphino)ethane,
1,2-bis(dimethylphosphino)-1,1-difluoroethane,
1,2-bis(dimethylphosphino)-1-fluoroethane,
1,2-bis(dimethylphosphino)propane,
1,2-bis(di(trifluoromethyl)phosphino)-1,1,2,2-tetrafluoroethane,
1,2-bis(di(trifluoromethyl)phosphino)propane,
2,3-bis(di(trifluoromethyl)phosphino)butane,
1,2-bis(di(trifluoromethyl)phosphino)butane,
1,3-bis(dimethylphosphino)butane,
1,3-bis(dimethylphosphino)propane,
1,3-bis(di(trifluoromethyl)phosphino)propane,
1,2-bis(dimethylphosphino)-1,1-dichloro-2,2-difluoroethane, and similar compounds wherein the phosphorus is replaced by nitrogen, arsenic, sulfur, oxygen, selenium, tellurium, or any other atom having a free electron pair, and the like.

Other useful target-seeking ligands include the alkylaminobis(difluorophosphine), i.e., RN(PF$_2$)$_2$, ligands and the like where R is an organic group, preferably an alkyl group having 1 to about 6 carbon atoms, an aryl group as phenyl, or the like, and substituted such groups; and the o-phenylene compounds such as, for example, orthophenylenebis(diarsine), orthophenylenebis(dimethylarsine), orthophenylenebis(diamine), orthophenylenebis(dimethylamine), orthophenylenebis(diphosphine), orthophenylenebis(dimethylphosphine), and the like.

Additional target-seeking ligands suitable for use in the present invention are those described by Nozzo et al., in *J. Amer. Chem. Soc.*, 101, p. 3683 (1979) and by Wilson et al., *J. Amer. Chem. Soc.*, 100, p. 2269 (1978), which are hereby incorporated by reference.

Any donor element can be used in the target-seeking ligand in accord with this invention provided that it is a neutral donor atom having a free-electron pair available for accepting a proton to provide a charged ligand and further provided that it has the capability of complexing with technetium (Tc-99 or Tc-99m) to form a cationic complex in the presence of suitable anions. Suitable such elements include, for instance, phosphorous (P), arsenic (As), nitrogen (N), oxygen (O), sulfur (S), antimony (Sb), selenium (Se), tellurium (Te), and the like. Preferred elements are P and As.

Accelerator compounds useful in the practice of the present invention are selected from the group of bidentate ligands capable of forming a four to six, preferably five member chelate ring with technetium. Preferably, such bidentate ligands also have the capability of reducing technetium. Bidentate ligands suitable as accelators for the practice of this invention include dicarboxylic acids, diphosphonic acids, enols, acidic 1,2-dihydroxy compounds, particularly 1,2-dihydroxy compounds having a nearby strongly electron-withdrawing group, alpha-hydroxycarboxylic acids, alpha-hydroxyphosphonic acids, and the like, etc. Specific examples of such accelerators include, for instance, catechol, oxalic acid, ascorbic acid, tartaric acid, hydroxymethylenediphosphonic acid, methylene diphosphonic acid, and the like, etc. Examples of electron-withdrawing groups suitable for use in such 1,2-dihydroxy compounds are $-NO_2$, $-Cl$, $-Br$, $-F$, $-I$, or $-CF_3$.

The compositions of this invention are useful for preparing radiodiagnostic agents wherein the target-seeking ligand is labelled with technetium. Labelling is accomplished by mixing a suitable quantity of $^{99m}$Tc-pertechnetate in solution with the accelerator compound and target-seeking ligand, and heating the admixture for a suitable length of time at a temperature attainable with a constant temperature water bath. Preferably, the heating step is performed at 100° C. for thirty minutes or less. An aqueous physiological saline solution is typically the solution of choice for labelling the target-seeking ligand because it is readily administered to the patient.

The compositions of this invention are preferably contained in a kit, such as a presterilized vial. The presterilized vial, such as a glass vial, containing the compositions of this invention is ready for use for preparing cationic technetium complexes for radiodiagnostic use. More preferably, the compositions are lyophilized in such kits to increase storage stability of the compositions. In such lyophilized kits, the target-seeking ligand is generally present as a water-soluble acid salt of the ligand.

The lyophilized kits are used by reconsituting with a suitable quantity of $^{99m}$Tc-pertechnetate in saline solution. The reconstituted compositions are then placed in a constant temperature water bath for a sufficient time to form labelled technetium complexes with the target-seeking ligand. Preferably, the reaction time is about 30 minutes or less at a temperature of about 100° C.

It has been found that lyophilized compositions for the preparation of cationic technetium complexes can be improved by the addition of a polyhydroxy-compound to the reaction mixture. The use of the polyhydroxy-compound, for reasons not fully understood, results in a more consistent yield of the cationic technetium complex. Preferred polyhydroxy-compounds include, for example, Hetastarch (hydroxyethyl starch), mannitol, glycerol, D-mannose, sorbitol, and the like.

To image the heart of a mannal, in-vivo, a radiopharmaceutical preparation in accord with the invention, having a suitable quantity of radioactivity for the particular mammal, is injected intravenously into the mammal. The mammal is positioned under a scintillation camera in such a way that the heart is covered by the field of view. High quality images of the heart are obtained analogous to those seen in clinical studies using Thallium-201.

In order to obtain high quality images the yield of radioactive labelled cationic technetium complex should preferably be greater than 70% after reconstituting the lyophilized mixture and labelling. Lower yields will result in poorer image quality and undesirable purification steps will be required to produce high quality images. This invention will be further illustrated by the examples that follow:

PREPARATION OF 1,2-BIS(DIMETHYLPHOSPHINO)ETHANE BIS-BISULFATE, i.e. DMPEH$_2^{2+}$. 2HSO$^-_4$ or DMPE.2H$_2$SO$_4$

Dissolve 470 mg of DMPE in 10 ml of ethanol in a 50 ml round-bottomed flask maintained under a nitrogen atmosphere. From a glass syringe, add, with stirring, 0.34 ml of concentrated sulfuric acid. After 10 minutes, filter the precipitate and recrystallize it from 10 ml. of methanol. Filter and dry under vacuum. 920 mg of a crystalline solid is obtained, which melts at 135–136.5° C. Structure and purity of the compound was confirmed by its infra-red and nuclear magnetic resonance spectra and elemental analysis.

COMPARATIVE EXAMPLE A

Dissolve 1 g mannitol, 150 mg sodium chloride, and 46 mg DMPE-bis(bisulfate) in 10 ml deoxyugenated physiological saline solution (0.15 Molar). Adjust the pH of the solution to 1.4 by adding the required volume of 2 N hydrochloric acid. Dispense 1 ml of the solution into each of several 10 cc vials, flushing each with nitrogen gas for 20 seconds, closing with a teflon-coated stopper and crimp-sealing it.

LABELLING PROCEDURE I

Inject 50 mCi of $^{99m}$Tc-pertechnetate in 0.5 ml physiological saline into each of several vials and place them in an oil bath, preheated and maintained at 150°±5° C., for 5–10 minutes. HPLC analyses show yields of 90 to 100%.

LABELLING PROCEDURE II

Inject 50 mCi of $^{99m}$Tc-pertechnetate in 0.5 ml physiological saline into each of several vials and place them in a steam autoclave preheated to 100° C. Set the temperature control to 135° C., and when that temperature is achieved, maintain it for 20 minutes. Allow the system to cool to 100° C. and remove the vials. HPLC analyses show yields of 95 to 100%.

COMPARATIVE EXAMPLE B

Dissolve 5 g mannitol and 230 mg DMPE-bis(bisulfate) in about 35 ml low-oxygen distilled water, and adjust the pH of the solution to 1.0 with 3 N sulfuric acid. Under cover of nitrogen, and with stirring, add low-oxygen distilled water gravimetrically, to a solution weight of 50 g. Dispense 1 ml of this solution into each of several 10 cc vials. Freeze-dry in keeping with procedures well-known to those skilled in the art, stoppering under nitrogen. Reconstitute each vial with 1 ml of physiological saline containing about 10–20 mCi $^{99m}$Tc-pertechnetate. Utilizing techniques similar to those of Example A above, autoclave for 30 minutes at 135° C. Thin layer chromatography (TLC) analyses show yields consistently greater than 95%.

COMPARATIVE EXAMPLE C

The procedure of Example B, above, was followed to prepare several vials except that the pH was adjusted to 2.0 and the amounts of reagents were changed so that each vial contained 0.336 mg DMPE.2H$_2$SO$_4$ and 20 mg mannitol.

The vials were used to label the DMPE.2H$_2$SO$_4$ according to the following procedures:

(1) Labelling with $^{99m}$Tc-pertechnetate as in Example A, above, but at 133° C. for 40 minutes yielded 90–95% labelled product.

(2) Labelling with $^{99m}$Tc-pertechnetate in 100° C. water bath for 30 minutes yielded ≦2% labelled product.

EXAMPLE 1

Oxalic Acid Dihydrate—DMPE.2H$_2$SO$_4$

Dissolve 1 g mannitol, 350 mg oxalic acid dihydrate, and 15.0 mg DMPE.2H$_2$SO$_4$ in 45 ml of low-oxygen distilled water and adjust the pH to 1.7 with 2N NaOH. Under cover of nitrogen, and with stirring, add low-oxygen distilled water gravemetrically to a solution weight of 50 g. Dispense 1 ml of this solution into each of several 3 cc vials. Freeze-dry in keeping with procedures well-known to those skilled in the art, stoppering under nitrogen. Reconstitute each vial with 1 ml of physiological saline containing 10–50 mCi $^{99m}$Tc-pertechnetate.

Place labelled vials in a boiling water bath at 100° C. for 30 minutes. TLC analyses show yields greater than 90%.

EXAMPLES 2–6

A formulation similar to example 1 but containing, per vial, 0.317 mg DMPE.2H$_2$SO$_4$, 8.5 mg oxalic acid dihydrate, 19.5 mg mannitol at pH=1.8 before lyophilization is labelled with 1.0 ml of physiological saline containing 55 mCi of $^{99m}$Tc-pertechnetate. After heating for 30 minutes at various temperatures, the yield of product analyzed by TLC was as shown in the following table.

| Example No. | Heating Temperature | % Product ± 10% |
|---|---|---|
| 2 | 60° C. | 23 |
| 3 | 70° C. | 68 |
| 4 | 80° C. | 89 |
| 5 | 90° C. | 96 |
| 6 | 100° C. | 97 |

EXAMPLE 7

Ascorbic Acid—DMPE.2H$_2$SO$_4$

A liquid formulation was prepared in physiological saline containing, per ml, 100 mg ascorbic acid, 1 mg DMPE.2H$_2$SO$_4$ at pH of 1.80. After labeling with $^{99m}$Tc-pertechnetate and heating 15 minutes at 100° C. the yield of product was 87%.

EXAMPLE 8

Imaging of Rabbit Heart Using Tl-201 (Prior Art)

2 mCi of Thallium-201 (as thallous chloride in physiological saline containing 0.9% benzyl alcohol) is injected intravenously into a 2.5 Kg male New Zealand Albino rabbit. The rabbit is positioned under a Searle Pho-Gamma scintillation camera in such a way that the heart and lung area are covered by the field of view. Approximately 10 minutes after injection, sufficient counts are accumulated to produce an image of the heart analogous to that seen in clinical studies of humans.

EXAMPLE 9

Imaging of Rabbit Heart Using $^{99m}$Tc-labelled Products with ≧80% Yield of Desired Labelled Complex Greater than 1 mCi of the $^{99m}$Tc-labelled product of Example 1 or 7 is injected into a rabbit and imaged as in Example 8. The quality and appearance of the heart image is similar to that obtained in Example 8.

EXAMPLE 10

Imaging of Baboon Heart Using $^{99m}$Tc-labelled Products with ≧80% of Desired Labelled Complex Greater than 10 mCi of the $^{99m}$Tc-labelled product of Example 1 or 7 is injected intravenously into an adult baboon positioned under a scintillation camera as was the rabbit in Example 8. Excellent quality images of the heart are obtained, which are equivalent to those characteristically obtained with Tl-201 in humans.

EXAMPLE 11

Visualization of Hepatobiliary Transit with $^{99m}$Tc-labelled Disofenin (Prior Art)

A lyophylized vial of HEPATOLITE ™ (New England Nuclear Corporation's brand of Technetium Tc99m Disofenin) is labelled with $^{99m}$Tc-pertechnetate in accordance with manufacturer's directions. At least 1 mCi of the labelled preparation is injected intravenously into a 2.5 Kg male New Zealand Albino rabbit. The rabbit is positioned under a Searle Pho-Gamma scintillation camera in such a way that the liver and gastro-intestinal tract are within the field of view. Sequential images taken from the time of injection demonstrate an initial liver uptake with gradual visualization of the gall bladder and gastro-intestinal tract, analogous to the diagnostically efficacious results obtained in clinical studies of normal healthy humans.

EXAMPLE 12

Visualization of Hepatobiliary Transit with $^{99m}$Tc-Labelled Products

Greater than 1 mCi of the $^{99m}$Tc-labelled product of Example 1 or 7 is injected into a rabbit as in Example 11. Sequential images of hepatobiliary transit reveals passage similar to that in Example 11, with comparable image quality of the liver and gall bladder.

EXAMPLE 13

Tartaric Acid—DMPE.2H$_2$SO$_4$

Lyophilized kits each consisting of a sealed vial containing 336 micrograms DMPE.2H$_2$SO$_4$ and 20 mg mannitol were used in this example. The kits were adjusted for pH so that when reconstituted with 1 ml physiological saline, they had a pH of 2.0 . To each freeze-dried kit was added 0.5 ml of physiological saline containing 15 mCi of $^{99m}$Tc-pertechnetate and 0.5 ml of physiological saline or 0.5 ml of physiological saline containing 0.2 M tartaric acid. After heating the kits for 30 minutes in a 100° C. water bath, TLC analysis showed the following yield of product, i.e. [$^{99m}$TC(DMPE)$_2$Cl$_2$]$^+$, and TcO$_2$.

| Tartaric Acid | % TcO$_2$ | % Product |
|---|---|---|
| 0 | 0 | 2 |

-continued

| Tartaric Acid | % TcO2 | % Product |
|---|---|---|
| 0.10 M | 0 | 20 |

EXAMPLE 14

Freeze-dried kits containing 1 mg of DMPE.2H$_2$SO$_4$ are reconstituted as in Example 13 except that catechol or methylenediphosphonic acid (MDP) are added to the reconstituted solution and the pH of the composition when reconstituted is 1.7. The kits are reconstituted with 10 mCi of $^{99m}$Tc-pertechnetate in saline, with accelerator added, and placed in a 100° C. water bath for 30 minutes and the yield of [$^{99m}$TC(DMPE)$_2$Cl$_2$]+ is as follows.

| Accelerator | % Product |
|---|---|
| Catechol (1 mg/ml) | 24 |
| MDP (10 mg/ml) | 30 |

EXAMPLE 15

50 microliters of (CH$_3$)$_2$PCH$_2$CH$_2$As(CH$_3$)$_2$ (ASP) was added to 50 ml of deoxygenated physiological saline having a pH adjusted to 1.0 with 1 N HCl. After the ASP was dissolved and 0.5 g oxalic acid added, the pH was adjusted to 1.5 with 1 N NaOH. One milliliter of the resulting solution was injected into each of several 5 cc vials which had been purged of oxygen and crimp-sealed. The ASP was labelled with 0.1 ml of saline containing 10 mCi of $^{99m}$Tc-pertechnetate, in a 100° C. water bath for 30 minutes. TLC analysis showed a yield of about 96% Tc-labelled ASP.

This invention has been described in detail with particular reference to the preferred embodiments thereof. However, it will be appreciated that those skilled in the art, upon reading this disclosure, may make modifications and improvements within the spirit and scope of the invention.

I claim:

1. A composition for preparing cationic lipophilic technetium complexes for radiodiagnostic imaging, said composition comprising an admixture of (a) an accelerator compound selected from the group of water-soluble organic bidentate ligands that are capable of coordinating with technetium to form a 4 to 6 member ring and (b) a target-seeking ligand or aqueous salt thereof, having the following structure:

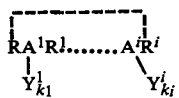

wherein:
i is an integer from 1 to 6;
R, R$^1$, R$^2$, R$^3$, R$^4$, R$^5$ and R$^6$ are each independently selected from hydrogen or substituted or unsubstituted alkyl, aryl, alkylaryl, arylalkyl, monocycloalkyl, polycycloalkyl, heterocyclic and carbocyclic groups, and R plus R$^i$ may be taken together to form a cyclic compound or separately to form a linear compound;
Y$^1$, Y$^2$, Y$^3$, Y$^4$, Y$^5$ and Y$^6$ are independently selected from substituted or unsubstituted alkyl, aryl, alkylaryl, arylalkyl, monocycloalkyl, polycycloalkyl, heterocyclic and carbocyclic groups;
A$^1$, A$^2$, A$^3$, A$^4$, A$^5$ and A$^6$ are each, independently, a neutral donor atoms having a free-electron pair available for complexing with TC-99m or TC-99 to form a cationic complex; and
k$_1$, k$_2$, k$_3$, k$_4$, k$_5$ and k$_6$ are each independently zero or one; or

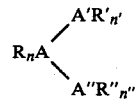

or

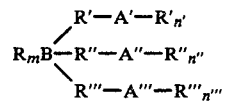

wherein:
R, R′, R″ and R‴ are independently selected from hydrogen or substituted or unsubstituted alkyl, aryl, alkylaryl, arylalkyl, monocycloalkyl, polycycloalkyl, heterocyclic and carbocyclic groups;
A, A′, A″ and A‴ are independently selected from the group of neutral donor atoms having a pair of electrons available for complexing with Tc-99m or TC-99 to form a cationic complex;
B is an atom selected from the group of neutral donor atoms having a pair of electrons available for complexing with Tc-99m or TC-99 or from the elements listed in Group IV A of the periodic table;
n, n′, n″ and n‴ are independently the integer 1 or 2; and
m is 0 or 1;
said accelerator compound having a weaker coordinating bond with technetium than the target-seeking ligand.

2. The composition of claim 1 wherein each A is selected from the group consisting of P, As, N, O, S, Sb, Se and Te.

3. The composition of claim 1 wherein said accelerator compound is capable of reducing technetium.

4. The composition of claim 1 wherein said accelerator is capable of coordinating with technetium to form a five member ring.

5. The composition of claim 1 wherein said accelerator compound is an alpha-hydroxy carboxylic acid.

6. The composition of claim 1 wherein said accelerator compound is an acidic 1,2-dihydroxy compound.

7. The composition of claim 6 wherein said accelerator compound is an enol, or a compound having a strong electron withdrawing group nearby the hydroxy groups so that the compound is acidic.

8. The composition of claim 7 wherein the electron withdrawing group is selected from —NO$_2$, —Cl, —Br, —F, —I, or —CF$_3$.

9. The composition of claim 1 wherein said target seeking ligand has the formula:

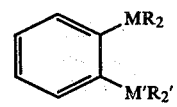

wherein M and M' are arsenic, phosphorus, nitrogen, sulfur, oxygen, selenium, tellurium, or any combination of them, and R and R' are independently hydrogen, an alkyl group having from 1 to about 6 carbon atoms, or an aryl group.

10. The composition of claim 1 wherein said target-seeking ligand has the formula:

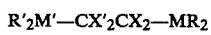

wherein M and M' are arsenic, phosphorus, nitrogen, sulfur, oxygen, selenium, tellurium, or any combination of them, and R and R' are independently hydrogen, an alkyl group having from 1 to about 6 carbon atoms, or an aryl group, and X and X' are independently selected from hydrogen, halide, or substituted or unsubstituted lower alkyl groups having 1 to about 6 carbon atoms.

11. The composition of claim 1 wherein said target-seeking ligand has the formula:

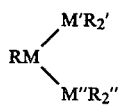

wherein M, M' and M" are independently selected from arsenic, phosphorous, nitrogen, sulfur oxygen, selenium, and tellurium, and R, R' and R" are independently selected from hydrogen, halide, an alkyl group having 1 to about 6 carbon atoms, or an aryl group.

12. The composition of claim 1 wherein said target-seeking ligand has the formula:

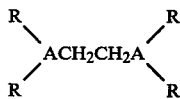

wherein A is P or As; and each R is independently H a lower alkyl group having from 1 to about 6 carbon atoms, or phenyl.

13. The composition of claim 1 wherein said target-seeking ligand has the formula:

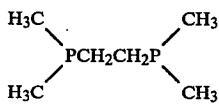

14. The composition of claim 1 wherein said target-seeking ligand has the formula:

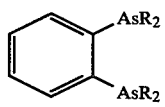

wherein R is H or a lower alkyl group having 1 to about 6 carbon atoms.

15. A method for making a cationic complex labelled with Tc-99m for radioscintigraphic imaging, said method comprising admixing $^{99m}$Tc-pertechnetate and the composition of any one of claims 1 through 14 and placing the resulting admixture in a constant temperature water bath for a period of time sufficient to form such labelled complex.

16. A lyophilized preparation comprising the composition of any one of claims 1 through 14.

17. A kit comprising a pre-sterilized, sealed vial containing the composition of any one of claims 1 through 14.

18. The kit of claim 17 wherein said composition is lyophilized.

19. The composition of claim 1 wherein said accelerator compound is selected from the group consisting of oxalic acid, ascorbic acid, tartaric acid, methylenediphosphonic acid, hydroxymethylenediphosphonic acid, or catechol.

20. The composition of claim 1 wherein said accelerator compound is a bidentate ligand capable of forming a five member chelate ring with technetium.

21. The composition of claim 1 wherein said accelerator compound is capable of reducing technetium.

22. The composition of claim 1 wherein said accelerator compound is a dicarboxylic acid.

23. The composition of claim 1 wherein said accelerator compound is a diphosphonic acid.

24. The composition of claim 1 wherein said accelerator compound is oxalic acid.

25. The composition of claim 1 wherein said accelerator compound is ascorbic acid.

26. The composition of any of claims 12, 13 or 14 wherein said accelerator compound is oxalic acid.

27. The composition of any of claims 12, 13 or 14 wherein said accelerator compound is ascorbic acid.

28. The composition of claim 1 wherein said target-seeking ligand is 1-dimethylphosphino-2-dimethylarseno-ethane.

29. A kit comprising a sterilized, sealed vial containing an admixture comprising oxalic acid or ascorbic acid and a target-seeking ligand having the structural formula

wherein each R is independently selected from the group consisting of hydrogen, an alkyl group from 1 to about 6 carbon atoms and an aryl group; and each A independently selected from arsenic or phosphorus; or an acid addition salt of said ligand.

30. The kit of claim 29 wherein said target-seeking ligand is bis(dimethylphosphino)ethane.

31. The kit of claim 29 wherein said admixture is lyophilized.

32. The kit of claim 31 wherein said target-seeking ligand is bis(dimethylphosphino)-ethane bis-bisulfate.

33. The kit of claim 31 wherein said target-seeking ligand is 1-dimethylphosphino-2-dimethylarseno-ethane bis-bisulfate.

* * * * *